(12) United States Patent
Locke et al.

(10) Patent No.: US 10,946,124 B2
(45) Date of Patent: Mar. 16, 2021

(54) HYBRID SEALING TAPE

(71) Applicant: KCI Licensing, Inc., San Antonio, TX (US)

(72) Inventors: Christopher Brian Locke, Bournemouth (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 591 days.

(21) Appl. No.: 14/517,521

(22) Filed: Oct. 17, 2014

(65) Prior Publication Data

US 2015/0119834 A1    Apr. 30, 2015

Related U.S. Application Data

(60) Provisional application No. 61/896,582, filed on Oct. 28, 2013.

(51) Int. Cl.
*A61F 13/02* (2006.01)
*A61M 1/00* (2006.01)
(Continued)

(52) U.S. Cl.
CPC ..... *A61M 1/0088* (2013.01); *A61F 13/00068* (2013.01); *A61F 13/025* (2013.01);
(Continued)

(58) Field of Classification Search
CPC .... A61F 13/00; A61F 13/00068; A61F 13/02; A61F 13/0216; A61F 13/0246;
(Continued)

(56) References Cited

U.S. PATENT DOCUMENTS 1,355,846 A   10/1920  Rannells
1,944,834 A    1/1934  Bennett
(Continued)

FOREIGN PATENT DOCUMENTS

AU    550575 A1    3/1986
AU    550575 B2    3/1986
(Continued)

OTHER PUBLICATIONS

International Search Report and Written Opinion for corresponding PCT application PCT/US2016/051768 dated Dec. 15, 2016.
(Continued)

*Primary Examiner* — Keri J Nelson

(57) ABSTRACT

A dressing for treating a tissue site with negative pressure is described. The dressing includes a tissue interface and a sealing member. The dressing further includes a sealing tape configured to be coupled to the sealing member and epidermis. The sealing tape includes a bonding adhesive and a sealing adhesive coupled to a side of the sealing tape. The sealing tape includes a layer of the bonding adhesive disposed on a film layer and a layer of sealing adhesive having one or more apertures disposed on the bonding adhesive. The sealing tape can include a layer of the bonding adhesive disposed on a portion of a film layer and a layer of the sealing adhesive disposed on a uncovered portions of the film layer.

22 Claims, 9 Drawing Sheets

(51) Int. Cl.
*A61F 13/00* (2006.01)
*B32B 37/12* (2006.01)
*A61L 15/58* (2006.01)

(52) U.S. Cl.
CPC ...... *A61F 13/0216* (2013.01); *A61F 13/0246* (2013.01); *A61F 13/0269* (2013.01); *A61L 15/58* (2013.01); *B32B 37/1292* (2013.01); *A61M 2207/00* (2013.01); *Y10T 156/10* (2015.01)

(58) Field of Classification Search
CPC ............... A61F 13/025; A61F 13/0269; A61F 2013/0089; A61F 2013/00421; A61F 2013/00536; A61F 2013/00561; A61F 2013/00655; A61M 1/0088
USPC ................. 602/52, 54, 55; 523/105, 111
See application file for complete search history.

(56) References Cited

U.S. PATENT DOCUMENTS

| | | |
|---|---|---|
| 2,547,758 A | 4/1951 | Keeling |
| 2,552,664 A | 5/1951 | Burdine |
| 2,632,443 A | 3/1953 | Lesher |
| 2,682,873 A | 7/1954 | Evans et al. |
| 2,860,081 A | 11/1958 | Eiken |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,183,116 A | 5/1965 | Schaar |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,903,882 A | 9/1975 | Augurt |
| 3,967,624 A | 7/1976 | Milnamow |
| 3,983,297 A | 9/1976 | Ono et al. |
| 4,060,081 A | 11/1977 | Yannas et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,174,664 A | 11/1979 | Arnott et al. |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,323,069 A | 4/1982 | Ahr et al. |
| 4,333,468 A | 6/1982 | Geist |
| 4,343,848 A | 8/1982 | Leonard, Jr. |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,146 A | 7/1986 | Ohno |
| 4,605,399 A | 8/1986 | Weston et al. |
| 4,608,041 A | 8/1986 | Nielsen |
| 4,617,021 A | 10/1986 | Leuprecht |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,025,783 A | 6/1991 | Lamb |
| 5,028,597 A | 7/1991 | Kodama et al. |
| 5,037,397 A | 8/1991 | Kalt et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,127,601 A | 7/1992 | Schroeder |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,244,457 A | 9/1993 | Karami et al. |
| 5,246,775 A | 9/1993 | Loscuito |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |

(56) References Cited

U.S. PATENT DOCUMENTS

| | | |
|---|---|---|
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,458,938 A | 10/1995 | Nygard et al. |
| 5,501,212 A | 3/1996 | Psaros |
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |
| 5,585,178 A * | 12/1996 | Calhoun ............... B32B 7/12 428/198 |
| 5,599,292 A | 2/1997 | Yoon |
| 5,607,388 A | 3/1997 | Ewall |
| 5,611,373 A | 3/1997 | Ashcraft |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,759,570 A | 6/1998 | Arnold |
| 5,776,119 A | 7/1998 | Bilbo et al. |
| 5,807,295 A | 9/1998 | Hutcheon et al. |
| 5,830,201 A | 11/1998 | George et al. |
| 5,878,971 A | 3/1999 | Minnema |
| 5,902,439 A | 5/1999 | Pike et al. |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,083,616 A | 7/2000 | Dressler |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,201,164 B1 | 3/2001 | Wulff et al. |
| 6,228,485 B1 | 5/2001 | Leiter |
| 6,238,762 B1 | 5/2001 | Friedland et al. |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,457,200 B1 | 10/2002 | Tanaka et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,197 B2 | 10/2012 | Eriksson et al. |
| 8,398,614 B2 | 3/2013 | Blott et al. |
| 8,449,509 B2 | 5/2013 | Weston |
| 8,529,532 B2 | 9/2013 | Pinto et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,632,523 B2 | 1/2014 | Eriksson et al. |
| 8,679,081 B2 | 3/2014 | Heagle et al. |
| 8,764,732 B2 | 7/2014 | Hartwell |
| 8,834,451 B2 | 9/2014 | Blott et al. |
| 8,920,830 B2 | 12/2014 | Mathies |
| 8,926,592 B2 | 1/2015 | Blott et al. |
| 9,017,302 B2 | 4/2015 | Vitaris et al. |
| 9,192,444 B2 | 11/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,877,873 B2 | 1/2018 | Coulthard et al. |
| 9,956,120 B2 | 5/2018 | Locke |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0090496 A1 | 7/2002 | Kim et al. |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0082925 A1 | 4/2004 | Patel |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0163278 A1 | 8/2004 | Caspers et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |

(56) References Cited

U.S. PATENT DOCUMENTS

| | | |
|---|---|---|
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0158442 A1 | 7/2005 | Westermann et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0014030 A1 | 1/2006 | Langen et al. |
| 2006/0020235 A1 | 1/2006 | Siniaguine |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0028526 A1 | 2/2007 | Woo et al. |
| 2007/0078366 A1 | 4/2007 | Haggstrom et al. |
| 2007/0161937 A1 | 7/2007 | Aali |
| 2007/0185426 A1 | 8/2007 | Ambrosio et al. |
| 2007/0190281 A1 | 8/2007 | Hooft |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2007/0283962 A1 | 12/2007 | Doshi et al. |
| 2008/0009812 A1 | 1/2008 | Riesinger |
| 2008/0027366 A1* | 1/2008 | Da Silva Macedo, Jr. .............. A61F 13/0203 602/47 |
| 2008/0090085 A1 | 4/2008 | Kawate et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0173389 A1 | 7/2008 | Mehta et al. |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216168 A1 | 8/2009 | Eckstein |
| 2009/0216170 A1 | 8/2009 | Robinson et al. |
| 2009/0216204 A1 | 8/2009 | Bhavaraju et al. |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326487 A1 | 12/2009 | Vitaris |
| 2009/0326488 A1 | 12/2009 | Budig et al. |
| 2010/0028390 A1 | 2/2010 | Cleary et al. |
| 2010/0030170 A1 | 2/2010 | Keller et al. |
| 2010/0063467 A1 | 3/2010 | Addison et al. |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1 | 6/2010 | Cotton |
| 2010/0168633 A1 | 7/2010 | Bougherara et al. |
| 2010/0168635 A1 | 7/2010 | Freiding et al. |
| 2010/0185163 A1 | 7/2010 | Heagle |
| 2010/0212768 A1 | 8/2010 | Resendes |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0268144 A1 | 10/2010 | Lu et al. |
| 2010/0286582 A1 | 11/2010 | Simpson et al. |
| 2010/0305490 A1 | 12/2010 | Coulthard et al. |
| 2010/0305524 A1 | 12/2010 | Vess et al. |
| 2010/0318072 A1 | 12/2010 | Johnston et al. |
| 2010/0324516 A1 | 12/2010 | Braga et al. |
| 2011/0046585 A1 | 2/2011 | Weston |
| 2011/0054423 A1 | 3/2011 | Blott et al. |
| 2011/0118683 A1 | 5/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0201984 A1 | 8/2011 | Dubrow et al. |
| 2011/0224631 A1 | 9/2011 | Simmons et al. |
| 2011/0229688 A1 | 9/2011 | Cotton |
| 2011/0244010 A1 | 10/2011 | Doshi |
| 2011/0257612 A1 | 10/2011 | Locke et al. |
| 2011/0257617 A1 | 10/2011 | Franklin |
| 2011/0281084 A1 | 11/2011 | Ashwell |
| 2011/0282309 A1 | 11/2011 | Adie et al. |
| 2012/0016322 A1 | 1/2012 | Coulthard et al. |
| 2012/0019031 A1 | 1/2012 | Bessert |
| 2012/0036733 A1 | 2/2012 | Dehn |
| 2012/0040131 A1 | 2/2012 | Speer |
| 2012/0059339 A1 | 3/2012 | Gundersen |
| 2012/0095380 A1 | 4/2012 | Gergely et al. |
| 2012/0109034 A1 | 5/2012 | Locke et al. |
| 2012/0123359 A1 | 5/2012 | Reed |
| 2012/0143157 A1 | 6/2012 | Riesinger |
| 2012/0237722 A1 | 9/2012 | Seyler et al. |
| 2012/0258271 A1 | 10/2012 | Maughan |
| 2012/0310186 A1 | 12/2012 | Moghe et al. |
| 2013/0030394 A1 | 1/2013 | Locke et al. |
| 2013/0053746 A1 | 2/2013 | Roland et al. |
| 2013/0066285 A1 | 3/2013 | Locke et al. |
| 2013/0096518 A1 | 4/2013 | Hall et al. |
| 2013/0098360 A1 | 4/2013 | Hurmez et al. |
| 2013/0116661 A1 | 5/2013 | Coward et al. |
| 2013/0150763 A1 | 6/2013 | Mirzaei et al. |
| 2013/0152945 A1 | 6/2013 | Locke et al. |
| 2013/0165887 A1 | 6/2013 | Mitchell et al. |
| 2013/0172843 A1 | 7/2013 | Kurata |
| 2013/0189339 A1 | 7/2013 | Vachon |
| 2013/0261585 A1 | 10/2013 | Lee |
| 2013/0304007 A1 | 11/2013 | Toth |
| 2013/0330486 A1 | 12/2013 | Shields |
| 2014/0039423 A1 | 2/2014 | Riesinger |
| 2014/0039424 A1 | 2/2014 | Locke |
| 2014/0058309 A1 | 2/2014 | Addison et al. |
| 2014/0107561 A1 | 4/2014 | Dorian et al. |
| 2014/0107562 A1 | 4/2014 | Dorian et al. |
| 2014/0141197 A1 | 5/2014 | Hill et al. |
| 2014/0155849 A1 | 6/2014 | Heaton et al. |
| 2014/0163491 A1 | 6/2014 | Schuessler et al. |
| 2014/0171851 A1 | 6/2014 | Addison |
| 2014/0178564 A1 | 6/2014 | Patel |
| 2014/0309574 A1 | 10/2014 | Cotton |
| 2014/0336557 A1 | 11/2014 | Durdag et al. |
| 2014/0350494 A1 | 11/2014 | Hartwell et al. |
| 2014/0352073 A1 | 12/2014 | Goenka |
| 2015/0030848 A1 | 1/2015 | Goubard |
| 2015/0045752 A1 | 2/2015 | Grillitsch et al. |
| 2015/0057625 A1 | 2/2015 | Coulthard |
| 2015/0080788 A1 | 3/2015 | Blott et al. |
| 2015/0080815 A1 | 3/2015 | Chakravarthy et al. |
| 2015/0119830 A1 | 4/2015 | Luckemeyer et al. |
| 2015/0141941 A1 | 5/2015 | Allen et al. |
| 2015/0190286 A1 | 7/2015 | Allen et al. |
| 2015/0290041 A1 | 10/2015 | Richard |
| 2016/0000610 A1 | 1/2016 | Riesinger |
| 2016/0067107 A1 | 3/2016 | Cotton |
| 2016/0144084 A1 | 5/2016 | Collinson et al. |

FOREIGN PATENT DOCUMENTS

| | | |
|---|---|---|
| AU | 745271 | 4/1999 |
| AU | 755496 | 2/2002 |
| AU | 745271 B2 | 3/2002 |

(56) References Cited

FOREIGN PATENT DOCUMENTS

| | | |
|---|---|---|
| AU | 755496 B2 | 12/2002 |
| AU | 2009200608 A1 | 10/2009 |
| CA | 2005436 | 6/1990 |
| CA | 2005436 A1 | 6/1990 |
| CN | 87101823 A | 8/1988 |
| DE | 26 40 413 A1 | 3/1978 |
| DE | 43 06 478 A1 | 9/1994 |
| DE | 29 504 378 U1 | 9/1995 |
| DE | 295 04 378 U1 | 10/1995 |
| DE | 202004018245 U1 | 7/2005 |
| DE | 202014100383 U1 | 2/2015 |
| EP | 097517 A1 | 1/1984 |
| EP | 0100148 A1 | 2/1984 |
| EP | 0117632 A2 | 9/1984 |
| EP | 0147119 A2 | 7/1985 |
| EP | 0161865 A2 | 11/1985 |
| EP | 0251810 A2 | 1/1988 |
| EP | 0275353 A2 | 7/1988 |
| EP | 0358302 A2 | 3/1990 |
| EP | 0538917 A1 | 4/1993 |
| EP | 0630629 A1 | 12/1994 |
| EP | 0659390 A2 | 6/1995 |
| EP | 0633758 B1 | 10/1996 |
| EP | 1002846 A1 | 5/2000 |
| EP | 1018967 A1 | 7/2000 |
| EP | 1018967 B1 | 8/2004 |
| EP | 2578193 A1 | 4/2013 |
| GB | 692578 | 6/1953 |
| GB | 692578 A | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 329 127 B | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 1961003393 | 2/1961 |
| JP | S62139523 U | 9/1987 |
| JP | S62-275456 A | 11/1987 |
| JP | 4129536 | 4/1992 |
| JP | 2005205120 A | 8/2005 |
| JP | 2007254515 A | 10/2007 |
| JP | 2008080137 A | 4/2008 |
| JP | 4129536 B2 | 8/2008 |
| JP | 2012050274 A | 3/2012 |
| NO | 2009/124100 A1 | 10/2009 |
| SG | 71559 | 3/1999 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01019306 A1 | 3/2001 |
| WO | 01/36188 A1 | 5/2001 |
| WO | 01/60296 A1 | 8/2001 |
| WO | 0168021 A1 | 9/2001 |
| WO | 0185248 | 11/2001 |
| WO | 0185248 A1 | 11/2001 |
| WO | 0190465 A2 | 11/2001 |
| WO | 01085248 A1 | 11/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2005123170 A1 | 12/2005 |
| WO | 2007022097 A2 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008026117 A1 | 3/2008 |
| WO | 2008041926 A1 | 4/2008 |
| WO | 2008048527 A2 | 4/2008 |
| WO | 2008054312 A1 | 5/2008 |
| WO | 2008/082444 A2 | 7/2008 |
| WO | 2008100440 A1 | 8/2008 |
| WO | 2008104609 A1 | 9/2008 |
| WO | 2008/131895 A1 | 11/2008 |
| WO | 2009/002260 A1 | 12/2008 |
| WO | 2008149107 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009126103 A2 | 10/2009 |
| WO | 2010011148 A1 | 1/2010 |
| WO | 2010016791 A1 | 2/2010 |
| WO | 2010032728 A1 | 3/2010 |
| WO | 2010/056977 A2 | 5/2010 |
| WO | 2010129299 A2 | 11/2010 |
| WO | 2011008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011130570 A1 | 10/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |
| WO | 2013066426 A2 | 5/2013 |
| WO | 2013090810 A1 | 6/2013 |
| WO | 2014022400 A1 | 2/2014 |
| WO | 2014039557 A1 | 3/2014 |
| WO | 2014078518 A1 | 5/2014 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |
| WO | 2017048866 A1 | 3/2017 |

OTHER PUBLICATIONS

International Search Report and Written Opinion for PCT/US2015/015493 dated May 4, 2015.
European Search Report for corresponding Application No. 15194949.2.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.

(56) References Cited

OTHER PUBLICATIONS

International Search Report and Written Opinion for PCT/US2015/029037 dated Sep. 4, 2015.
International Search Report and Written Opinion dated Jun. 1, 2011 for PCT International Application No. PCT/US2011/028344.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report dated May 22, 2014 for EP.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
Partial Internationl Search Report dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion dated Jan. 5, 2010; PCT International Application No. PCT/US2009/057130.
Response filed Oct. 20, 2011 for U.S. Appl. No. 12/398,904.
Interview Summary dated Oct. 27, 2011 for U.S. Appl. No. 12/398,904.
Non-Final Office Action dated Jul. 20, 2011 for U.S. Appl. No. 12/398,904.
V.A. Solovev et al., Guidelines, The Method of Treatment of Immagure External Fistulas in the Upper Gastrointestinal Tract, editor-in-chief Prov. V.I. Parahonyak (S.M. Kirov Gorky State Medican Institute, Gorky, U.S.S.R. 1987) ("Solovev Guidelines").
V.A. Kuznetsov & N.a. Bagautdinov, "Vacuum and Vacuum-Sorption Treatement of Open Septic Wounds," in All-Union Conference on Wounds and Wound Infections: Presentation Abstracts, edited by B.M. Kostyuchenok et al. (Mosco, U.S.S.R. Oct. 28-29, 1986) pp. 91-92 ("Bagautdinov II").
V.A. Solovev, Dissertation Abstract, Treatement and Prevention of Suture Failures after Gastric Resection (S.M. Kirov Gorky State Medical Institute, Gorky, U.S.S.R. 1998 ("Solovev Abstract").
NDP 1000 Negative Pressure Wound Terapy System, Kalypto Medical, pp. 1-4.
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
Response to Non-Final Rejection for U.S. Appl. No. 12/398,904, filed Jun. 4, 2012.
International Search Report and Written Opinion for PCT/US2014/061251 dated May 8, 2015.
International Search Report and Written Opinion for PCT/IB2013/060862 dated Jun. 26, 2014.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A. et al; "Vacuum Therapy in the Treatment of Purulent Lactation Mastitis"; Vestnik Khirurgi, May 14, 1986, pp. 66-70, and 9 pages English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

(56) References Cited

OTHER PUBLICATIONS

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E. M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

M. Waring et al., "Cell attachment to adhesive dressing: qualitative and quantitative analysis", Wounds, UK, (2008), vol. 4, No. 3, pp. 35-47.

R. White, "Evidence for atraumatic soft silicone wound dressing use". Wound, UK (2005), vol. 3, pp. 104-108, Mepilex Border docs, (2001).

European Search Report for corresponding application 17183683.6, dated Sep. 18, 2017.

European Search Report for corresponding application 17164033.7, dated Oct. 13, 2017.

Extended European Search Report for corresponding application 17191970.7, dated Oct. 26, 2017.

European Search Report for corresponding EP Application 171572787 dated Jun. 6, 2017.

International Search Report and Written Opinion for corresponding application PCT/US2016/031397, dated Aug. 8, 2016.

European Search Report for corresponding application 17167872.5, dated Aug. 14, 2017.

Office Action for related U.S. Appl. No. 13/982,650, dated Dec. 14, 2017.

Australian Office Action for related application 2013344686, dated Nov. 28, 2017.

Office Action for related U.S. Appl. No. 14/490,898, dated Jan. 4, 2018.

International Search Report and Written Opinion for related application PCT/US2017/058209, dated Jan. 10, 2018.

Office Action for related U.S. Appl. No. 14/965,675, dated Jan. 31, 2018.

Office Action for related U.S. Appl. No. 14/965,675, dated Aug. 9, 2018.

Office Action for related U.S. Appl. No. 15/307,472, dated Oct. 18, 2018.

Extended European Search Report for related application 17177013.4, dated Mar. 19, 2018.

Extended European Search Report for related application 16793298.7, dated Mar. 27, 2018.

Office Action for related U.S. Appl. No. 14/965,675, dated Dec. 12, 2018.

Office Action for related U.S. Appl. No. 14/619,714, dated Dec. 3, 2018.

Office Action for related U.S. Appl. No. 14/630,290, dated Jan. 11, 2019.

Office Action for related U.S. Appl. No. 15/265,718, dated Feb. 7, 2019.

Office Action for related U.S. Appl. No. 15/410,991, dated May 2, 2019

Extended European Search Report for related application 18193559.4, dated Dec. 17, 2018.

Office Action for related U.S. Appl. No. 14/080,348, dated Apr. 12, 2019.

Japanese Notice of Rejection for related application 2016-570333, dated Feb. 26, 2019.

Office Action for U.S. Appl. No. 15/314,426, dated Aug. 29, 2019.

Office Action for related U.S. Appl. No. 15/600,451, dated Nov. 27, 2019.

Australian Office Action for related application 2018278874, dated Feb. 12, 2020.

Office Action for related U.S. Appl. No. 14/630,290, dated Apr. 30, 2020.

Office Action for related U.S. Appl. No. 15/793,044, dated May 13, 2020.

EP Informal Search Report for related application 19186600.3, received May 11, 2020.

Office Action for related U.S. Appl. No. 15/884,198, dated May 19, 2020.

Office Action for related U.S. Appl. No. 16/007,060, dated Aug. 18, 2020.

Office Action for related U.S. Appl. No. 15/937,485, dated Aug. 4, 2020.

Office Action for related U.S. Appl. No. 15/793,044, dated Sep. 24, 2020.

Extended European Search Report for related application 20185730.7, dated Oct. 9, 2020.

(56) References Cited

OTHER PUBLICATIONS

Advisory Action for related U.S. Appl. No. 15/793,044, dated Dec. 9, 2020.

* cited by examiner

HYBRID SEALING TAPE

RELATED APPLICATION

This application claims the benefit, under 35 USC § 119(e), of the filing of U.S. Provisional Patent Application Ser. No. 61/896,582, entitled "HYBRID DRAPE STRIPS," filed Oct. 28, 2013, which is incorporated herein by reference for all purposes.

FIELD

The present disclosure relates generally to dressings for adhering to a patient, and more particularly, but without limitation, to a hybrid sealing tape having at least two adhesives disposed thereon.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with negative pressure is commonly referred to as "negative-pressure therapy," but may also be known by other names, including "negative pressure wound therapy," "reduced-pressure therapy," and "vacuum therapy," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

SUMMARY

According to an illustrative, non-limiting embodiment, a dressing for treating a tissue site with negative pressure is described. The dressing may include a tissue interface configured to be positioned adjacent to the tissue site. The dressing also may include a sealing member configured to be positioned over the tissue interface and the tissue site to form a sealed environment. The dressing further may include one or more sealing tape configured to be coupled to the sealing member and epidermis adjacent to the tissue site. The sealing tape each may have a bonding adhesive and a sealing adhesive coupled to a side of each sealing tape.

According to another illustrative embodiment, a system for treating a tissue site with negative-pressure is described. The system may include a manifold configured to be positioned adjacent to the tissue site and a drape configured to be positioned over the tissue site and the manifold and configured to seal to tissue adjacent to the tissue site to form a sealed space. The system also may include a negative-pressure source configured to provide negative-pressure to the sealed space. The system further may include one or more sealing tape configured to be coupled to the drape and epidermis adjacent to the tissue site. The sealing tape may each have a bonding adhesive and a sealing adhesive coupled to a side of each sealing tape.

According to another illustrative embodiment, a method for treating a tissue site with negative-pressure is described. A manifold may be disposed adjacent to the tissue site. The manifold may be covered with a drape and the drape may be sealed to tissue adjacent to the tissue site to form a sealed space. A negative-pressure source may be configured to provide negative-pressure to the sealed space. One or more sealing tape may be coupled to the drape and epidermis adjacent to the tissue site. The sealing tape may each have a bonding adhesive configured to form a bonding coupling and a sealing adhesive configured to form a sealing coupling coupled to a side of the sealing tape.

According to yet another illustrative embodiment, a method for manufacturing sealing tape for a negative-pressure system is described. The method provides a film layer and couples a layer of a bonding adhesive to the film layer. The method couples a layer of a sealing adhesive to the bonding layer. The method removes portions of the sealing adhesive to form a first pattern and expose the bonding adhesive through the sealing adhesive in a second pattern.

According to still another illustrative embodiment, a method for manufacturing sealing tape for a negative-pressure system is described. A film layer may be provided and a bonding adhesive may be disposed on a first portion of the film layer in a first pattern. A sealing adhesive may be disposed on a second portion of the film layer in a second pattern. The second pattern may be registered with the first pattern so that the first portion and the second portion cover substantially different portions of the film layer.

Other aspects, features, and advantages of the illustrative embodiments will become apparent with reference to the drawings and detailed description that follow.

BRIEF DESCRIPTION OF THE DRAWINGS

Illustrative embodiments are described in detail below with reference to the attached drawings, which are incorporated by reference herein, and wherein.

DETAILED DESCRIPTION

New and useful systems, methods, and apparatuses associated with drapes used for regulating pressure are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The example embodiments may also be described herein in the context of negative-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive negative-pressure therapy. However, as should be recognized by those skilled in the art, this frame of reference is merely a descriptive expedient rather than a strict prescription.

Figure 1A:
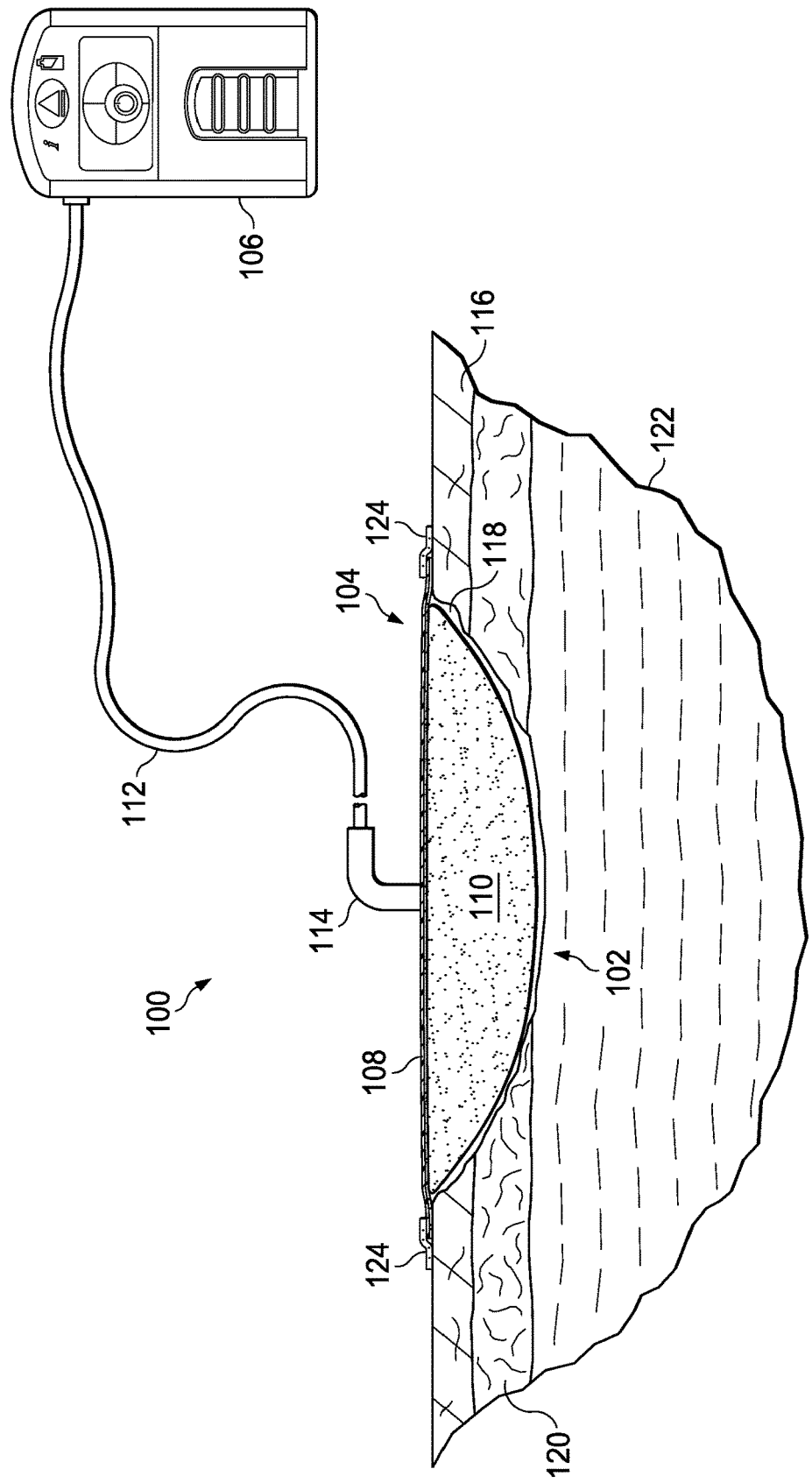
FIG. 1A is a schematic diagram (with a portion shown in elevation) of an illustrative embodiment of a system for treating a tissue site on a patient with negative pressure that may be associated with some illustrative embodiments of the system.

FIG. 1A is a sectional view of an example embodiment of a negative-pressure therapy system 100 illustrating details that may be associated with some embodiments for treating a tissue site 102 with negative pressure. As shown in the illustrative embodiment of FIG. 1A, the negative-pressure therapy system 100 may include a dressing 104 fluidly coupled to a negative-pressure source 106. In some embodiments, the negative-pressure source 106 may be fluidly coupled to the dressing 104 by a conduit, such as a tube 112, and a connector, such as a connector 114. The dressing 104 may generally include a cover or sealing member, such as a drape 108, and a tissue interface, such as a tissue interface 110. The drape 108 may be attached to an epidermis 116. The drape 108 can substantially prevent the leakage of fluids while allowing vapor to egress through the drape 108. In some embodiments, the dressing 104 may include one or more sealing tape 124 coupled to epidermis 116 and the drape 108.

In general, components of the negative-pressure therapy system 100 may be coupled directly or indirectly to each other. For example, the negative-pressure source 106 may be directly coupled to the connector 114 and indirectly coupled to the tissue interface 110 through the connector 114. Components may be fluidly coupled to each other to provide a path for transferring fluids (i.e., liquid and/or gas) between the components.

In some embodiments, components may be fluidly coupled with a tube, such as the tube 112, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, a tissue interface, such as the tissue interface 110, may be placed within, over, on, against, or otherwise proximate to a tissue site. The drape 108 may be sealed to undamaged epidermis peripheral to the tissue site. Thus, the drape 108 can provide a sealed therapeutic environment 118 proximate to the tissue site 102. The sealed therapeutic environment 118 may be substantially isolated from the external environment, and the negative-pressure source 106 can reduce the pressure in the sealed therapeutic environment 118. Negative pressure applied across the tissue site through a tissue interface in the sealed therapeutic environment 118 can induce macrostrain and microstrain in the tissue site 102, as well as remove exudates and other fluids from the tissue site. The removed exudates and other fluids can be collected in a container and disposed of properly.

The fluid mechanics of using a negative-pressure source to reduce pressure in another component or location, such as within a sealed therapeutic environment 118, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a negative-pressure source, and conversely, the term "upstream" implies a position relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, a fluid path may also be reversed in some applications, such as by substituting a positive-pressure source for a negative-pressure source, and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location. In some embodiments, the tissue site 102 may be a wound that extends through the epidermis 116, through a dermis 120, and into subcutaneous tissue 122.

"Negative pressure" generally refers to a pressure less than a local ambient pressure, such as the ambient pressure in a local environment external to the sealed therapeutic environment 118 provided by the drape 108. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 106, may be a reservoir of air at a negative pressure, or may be a manual or electrically-powered device that can reduce the pressure in a sealed volume, such as a vacuum pump, a suction pump, a wall-suction port available at many healthcare facilities, or a micro-pump, for example. A negative-pressure source may be housed within or used in conjunction with other components, such as sensors, processing units, alarm indicators, memory, databases, software, display devices, or operator interfaces that further facilitate negative-pressure therapy. While the amount and nature of negative pressure applied to a tissue site may vary according to therapeutic requirements, the pressure is generally a low vacuum, also commonly referred to as a rough vacuum between −5 mm Hg (−667 Pa) and −500 mm Hg (−66.7 kPa). Common therapeutic ranges are between −75 mm Hg (−9.9 kPa) and −300 mm Hg (−39.9 kPa).

The tissue interface 110 can be generally adapted to contact a tissue site. The tissue interface 110 may be partially or fully in contact with the tissue site. If the tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to distribute negative pressure across a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment 118 is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 108 is an example of a sealing member. A sealing member may be constructed from a material that can provide a fluid seal between two environments or components, such as between a therapeutic environment and a local external environment. A sealing member may be, for example, an impermeable or semi-permeable, elastomeric film or barrier that can provide a seal adequate to maintain a negative pressure at a tissue site for a given negative-pressure source. For semi-permeable materials, the permeability generally should be low enough that a desired negative pressure may be maintained. Generally, a drape suitable for covering a tissue site for negative-pressure therapy may comprise a film having a thickness between about 25 microns and about 50 microns that is water-vapor permeable and formed of a polymer. The film, often formed of polyurethane, may be coated with an adhesive having a coating weight between about 25 gsm and about 65 gsm. The adhesive may often be acrylic-based and pressure sensitive. A pressure-sensitive adhesive increases in bond strength when pressed against the surface to which the adhesive is being bonded. In some applications, a pressure-sensitive adhesive may undergo a physical change when compressed against a surface. In other applications, a pressure-sensitive adhesive may flow into crevices of a surface when compressed, increasing the bond strength without undergoing a physical change.

An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion, or an entire sealing member. In some embodiments, the attachment device may be an acrylic-based pressure sensitive adhesive having a coating weight between about 25 grams/m² (gsm) and about 60 gsm. Other example embodiments of an attachment device may include a double-sided tape, paste, hydrocolloid, hydrogel, silicone gel, organogel, or an acrylic adhesive.

A "container" broadly includes a canister, pouch, bottle, vial, or other fluid collection apparatus. A container, for example, can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A connector 114 may be used to fluidly couple the tube 112 to the sealed therapeutic environment 118. The negative pressure developed by the negative-pressure source 106 may be delivered through the tube 112 to the connector 114. In one illustrative embodiment, the connector 114 may be a T.R.A.C.® Pad or Sensa T.R.A.C.® Pad available from KCI of San Antonio, Tex. The connector 114 allows the negative pressure to be delivered to the sealed therapeutic environment 118. In other exemplary embodiments, the connector 114 may also be a tube inserted through the drape 108. The negative pressure may also be generated by a device directly coupled to the drape 108, such as a micropump.

The provision of negative-pressure therapy with negative-pressure therapy systems, such as the negative-pressure therapy system 100, is increasingly being performed with smaller therapy devices that use battery power rather than a connection to an electrical outlet. Use of battery power decreases the total power supply available to a therapy device. As a result, power drains that would be considered negligible in a device powered through an electrical outlet connection may significantly reduce the ability of the therapy device to provide therapy. A power drain refers to operation of the therapy device that requires use of electrical power, for example, operation of a pump to generate negative pressure. Power drains may be caused by low-level dressing leaks, for example. A low-level dressing leak can drain power from a battery of a therapy device by repeatedly triggering operation of the therapy device to maintain the necessary negative pressure at the tissue site. Power drains can shorten the useful life of the therapy device by draining the device battery faster, requiring more frequent disposal of the device, recharging of the battery, or battery replacement. Leak detection techniques may help to identify some leaks that may be sealed by the user; however, low-level leaks will challenge the most sensitive leak detection systems and may often go undetected.

Low-level dressing leaks may occur between a drape and epidermis surrounding a tissue site if the drape fails to completely seal to the epidermis. Generally, a drape may include an adhesive having a strength sufficient to seal against leaks but that may also cause pain to a patient if the drape is removed. A drape using an acrylic adhesive as described above is generally suitable for a dressing if a negative-pressure source powered by a continuous power supply can compensate for a leak.

Some drapes may use a bonding adhesive an alternative to an acrylic adhesive. A bonding adhesive may have a bond strength that is greater than the bond strength of the standard acrylic adhesive. A bonding adhesive may be better for sealing than a standard acrylic adhesive, but the bond strength would cause significantly more discomfort if the drape is removed. In addition, removing a drape having a bonding adhesive may cause significant damage to patients having delicate or damaged skin.

A drape that has a sealing adhesive can fill gaps between the drape and the epidermis to limit leaks and can be easy to remove with low discomfort to the patient. Various sealing, gap-filling adhesives, such as silicone, hydrocolloids, and hydrogels, have been tried but each has drawbacks. For example, hydrogel adhesives are usually low tack and prone to swelling, creep, and mobility when used with fluid systems. Available hydrogels and hydrocolloids do not adhere well and may move when anchored. In another example, silicone adhesives can fill gaps and seal, but are not breathable and may lose the necessary mechanical bonding strength as the silicone adhesives interact with moisture during use.

A hybrid drape having a thick sealing layer that is perforated and laminated over an adhesive coated film can overcome many of these challenges. For example, a hybrid drape may include a film layer having a bonding adhesive applied directly to the film layer, and a sealing adhesive applied directly to the bonding adhesive. The sealing adhesive can be perforated to expose the bonding adhesive. When the drape is applied to a patient, the bonding adhesive can be pushed through the perforations of the sealing adhesive to secure the sealing adhesive to the patient. This laminated configuration may provide the benefits of the sealing adhesive and the bonding adhesive over the entire drape area. For example, the laminated configuration can seal typical low-level leaks and mechanically affix to the epidermis without secondary processes. The laminated configuration may also require minimal additional application care by the user and can be removable with minimal trauma to the patient. However, construction of the laminated configuration requires additional assembly steps and an increase in materials that may significantly increase costs.

Other hybrid drapes may register a bonding adhesive and a sealing adhesive. These hybrid drapes apply both the bonding adhesive and the sealing adhesive directly to a film layer. The bonding adhesive and the sealing adhesive may each cover different portions of the film layer to reduce the overall thickness of the hybrid drape and decrease the amount of adhesive needed to construct the hybrid drape. However, the complexity of the manufacturing process may also have increased costs relative to a non-hybrid drape.

For some negative-pressure therapies, a standard drape having a standard acrylic adhesive may be used while treatment occurs in a care facility, such as a hospital. The negative-pressure therapy may be performed using a wall-powered negative-pressure source. Often, a patient may be discharged from a care facility before negative-pressure therapy concludes. Negative-pressure therapy may continue outside of the care facility using a portable negative-pressure source. A hybrid drape may be applied to address leaking issues that may arise with a portable negative-pressure source. However, it may be disadvantageous to change the dressing during the transition. For example, changing the dressing may increase the cost of negative-pressure therapy by requiring additional dressings to be used. Changing the dressing may also cause additional irritation to the tissue site, which may negatively impact healing of the tissue site and patient comfort.

As disclosed herein, the negative-pressure therapy system 100 can overcome these challenges and others by providing the sealing tape 124 having a hybrid adhesive configuration. In some embodiments, the sealing tape 124 may have two adhesives, a bonding adhesive and a sealing adhesive. As shown in FIG. 1A, the sealing tape 124 may be applied to the drape 108 so that the sealing tape 124 may partially couple to the drape 108 and partially couple to the epidermis 116, covering an edge of the drape 108. The sealing tape 124 may provide increased sealing of the drape 108 to the epidermis 116.

Figure 1B:
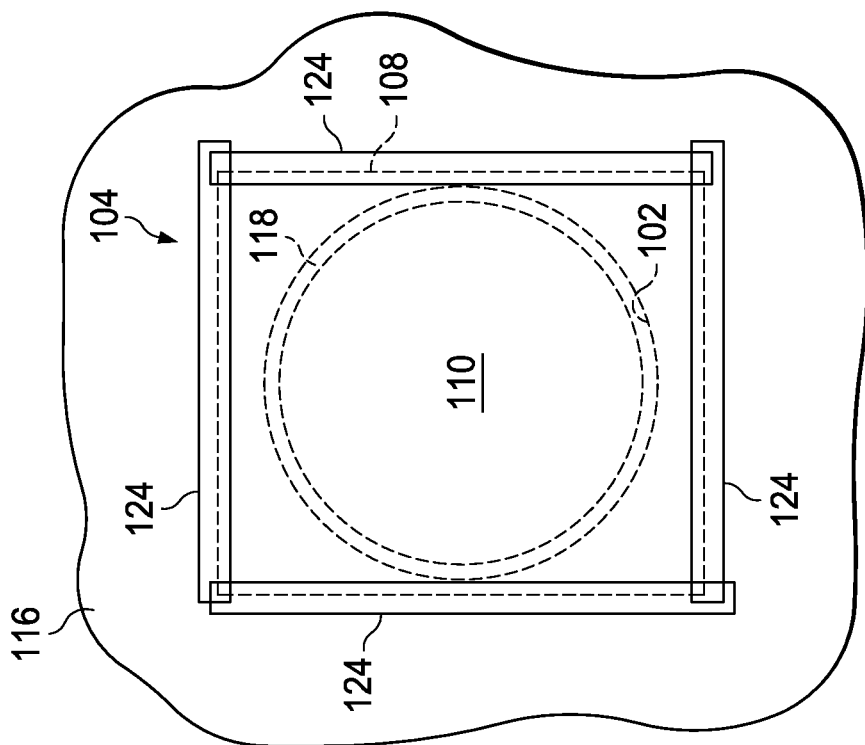
FIG. 1B is a plan view of a portion of the system of FIG. 1A.

FIG. 1B is a plan view of the dressing 104 illustrating additional details that may be associated with some embodiments. As shown, the tissue interface 110 may be disposed at the tissue site 102 and covered with the drape 108 to form the sealed therapeutic environment 118. The sealing tape 124 may be positioned to cover edges of the drape 108. In some embodiments, the sealing tape 124 may be partially coupled to the drape 108 and partially coupled to the epidermis 116. In some embodiments, ends of the sealing tape 124 may overlap one another.

Figure 2B:
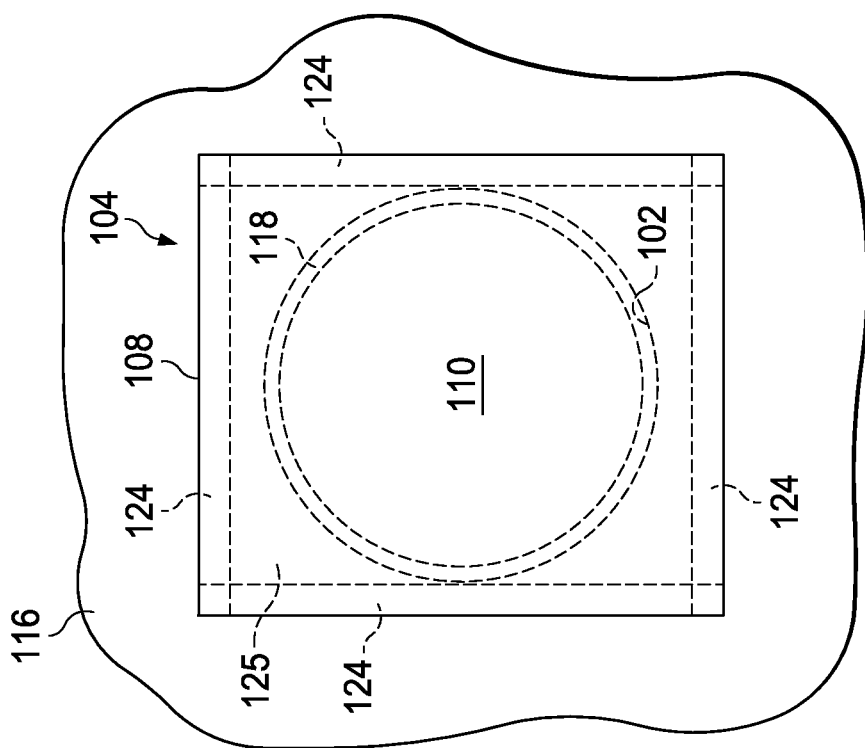
FIG. 2B is a plan view of a portion of the system of FIG. 2A.
Figure 2A:
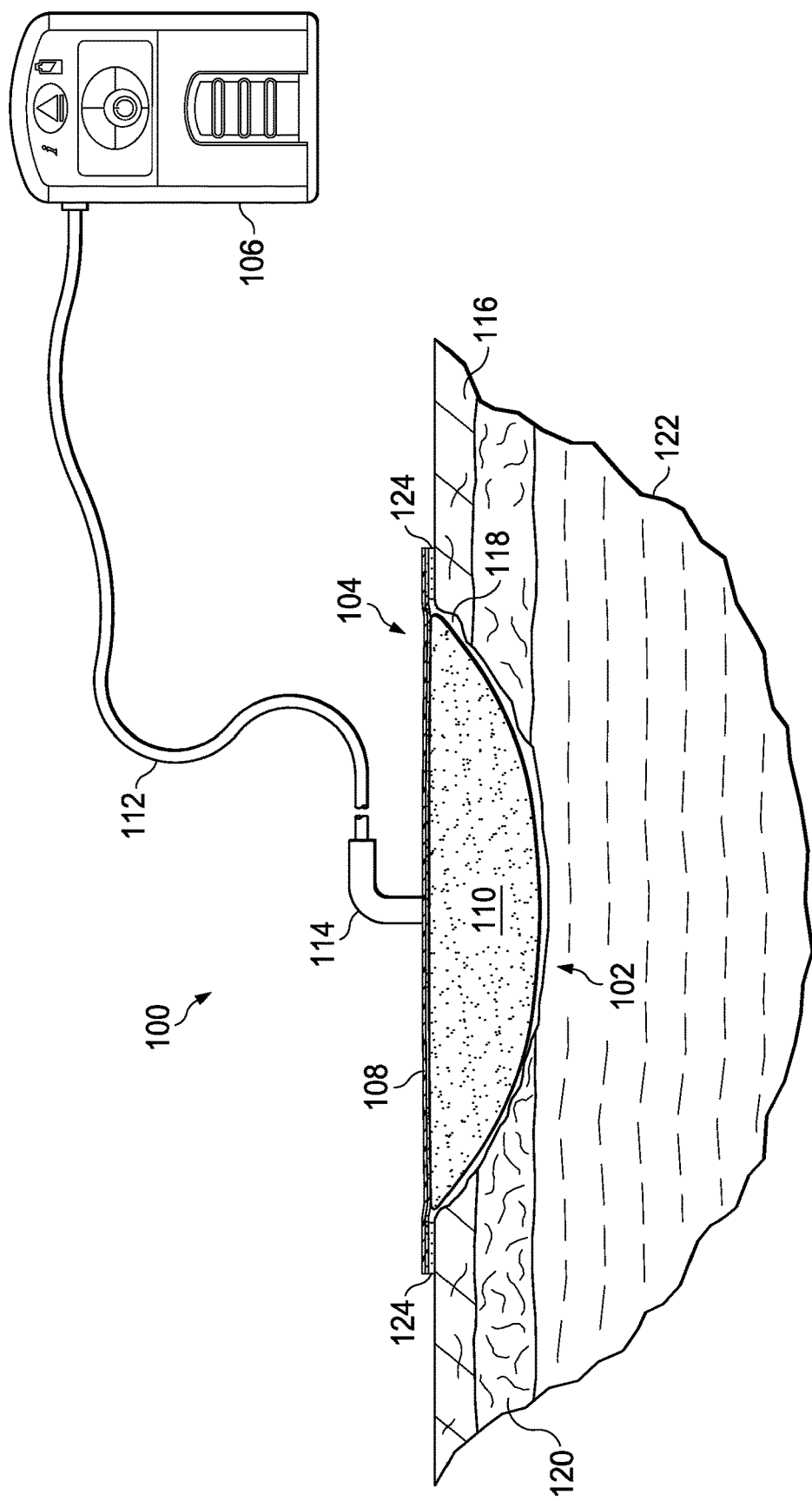
FIG. 2A is a schematic diagram (with a portion shown in elevation) of another illustrative embodiment of a system for treating a tissue site on a patient with negative pressure.

FIG. 2A is a sectional view of the negative-pressure therapy system 100 for treating the tissue site 102 with negative pressure illustrating details that may be associated another embodiment. In some embodiments, the sealing tape 124 may be applied directly to the epidermis 116 adjacent to the tissue site 102. The drape 108 may be coupled directly to the sealing tape 124. The sealing tape 124 may provide a stronger bond to the epidermis 116 and a better surface for the drape 108 to seal to, decreasing the size of the leaks through the dressing 104. The drape 108 may bond directly to a surface of the sealing tape 124 opposite the epidermis 116. The surface of the sealing tape 124 may be formed of a material to which the standard adhesive of the drape 108 may bond to more readily than the epidermis 116. In addition, the surface of the drapes strips 124 may have fewer crevices, bumps, and cracks than the epidermis 116, providing a better bonding surface for the drape 108.

FIG. 2B is a plan view of the dressing 104 illustrating additional details that may be associated with some embodiments. As shown, the tissue interface 110 may be disposed at the tissue site 102. The sealing tape 124 may be disposed around the tissue site 102 to form a window 125, the tissue site 102 being within boundaries of the window 125. In some embodiments, the window 125 may be an area of tissue having peripheral portions bounded by the sealing tape 124. In some embodiments, four sealing tape 124 may be disposed on the epidermis 116 so that the window 125 has a square shape having the tissue site 102 within the window 125. In other embodiments, more or fewer sealing tape 124 may be used as needed and may form other shapes. In some embodiments, the sealing tape 124 may couple directly to the epidermis 116. The drape 108 may then be coupled at least to the sealing tape 124 to cover the tissue site 102 and the tissue interface 110 to form the sealed therapeutic environment 118. In some embodiments, ends of the sealing tape 124 may overlap. In other embodiments, the sealing tape 124 may be cut so that ends of the sealing tape 124 do not overlap.

Figure 3:
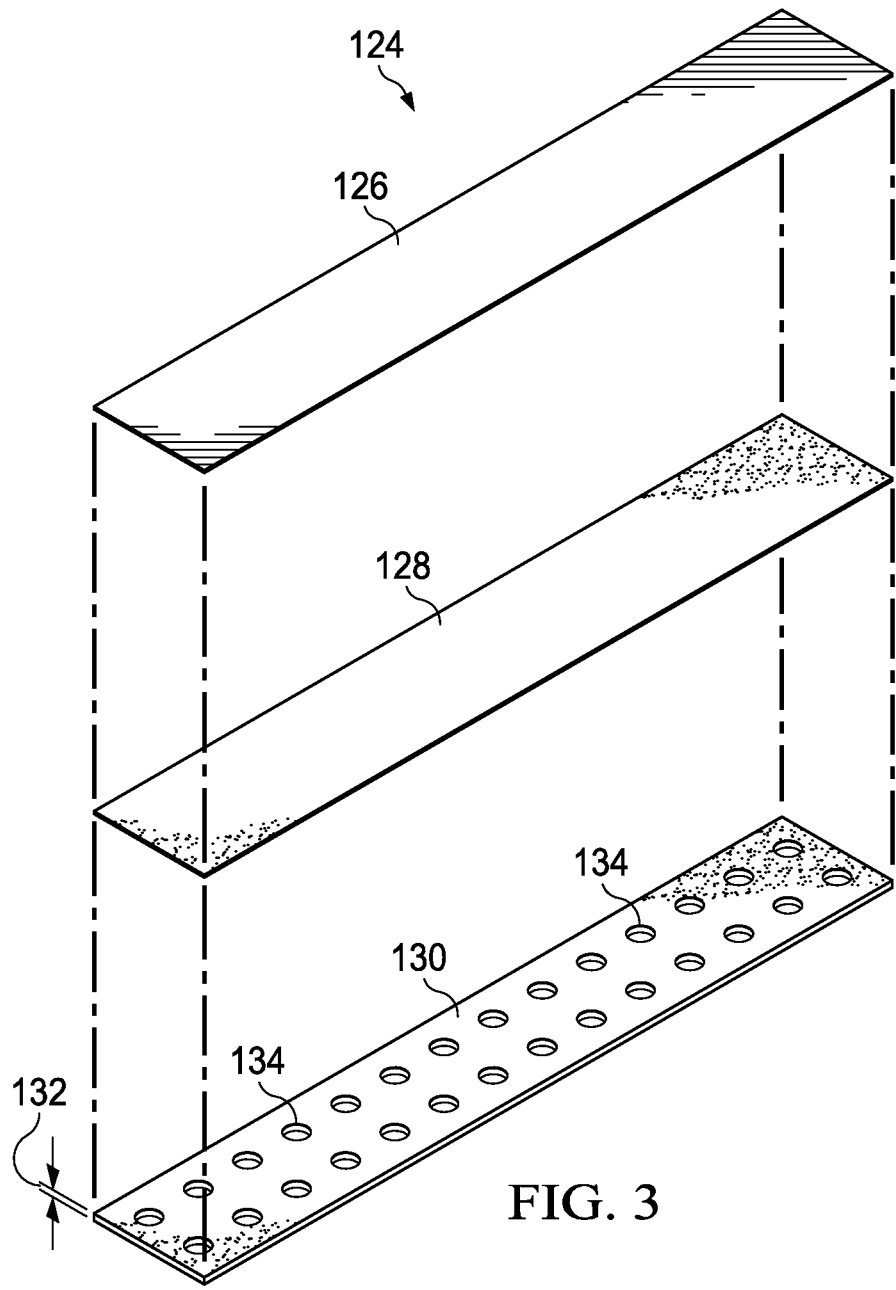
FIG. 3 is an exploded perspective view of a sealing tape that may be used with some embodiments of the systems of FIG. 1A and FIG. 2A.

FIG. 3 is an exploded perspective view of the sealing tape 124, illustrating details that may be associated with some embodiments. In some embodiments, the sealing tape 124 may include a film layer 126, a layer of a bonding adhesive 128, and a layer of a sealing adhesive 130. The film layer 126 may be liquid-impermeable and vapor-permeable, that is, the film layer 126 may allow vapor to egress and inhibit liquids from exiting. The film layer 126 may be a flexible film that is breathable and may have a high moisture vapor transfer rate (MVTR), for example, greater than or equal to about 300 g/m$^2$/24 hours. The film layer 126 may be formed from a range of medically approved films ranging in thickness typically from about 15 microns (μm) to about 50 microns (μm). In other embodiments, a drape having a low MVTR or that allows no vapor transfer might be used. In some embodiments, the film layer 126 can also function as a barrier to liquids and microorganisms.

The film layer 126 may be formed from numerous materials, such as one or more of the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. In some embodiments, the film layer 126 may be formed from a breathable cast matt polyurethane film sold by Expopack Advanced Coatings of Wrexham, United Kingdom, under the name INSPIRE 2301. The illustrative film may have an MVTR (inverted cup technique) of 14400 g/m$^2$/24 hours and may be approximately 30 microns thick.

The bonding adhesive 128 may be coupled directly to the film layer 126. In some embodiments, the bonding adhesive 128 and the film layer 126 may be coextensive. In other embodiments, the bonding adhesive 128 and the film layer 126 may not be coextensive. A bonding adhesive may be a medically-acceptable, pressure-sensitive adhesive. For example, a bonding adhesive may be formed from an acrylic adhesive, rubber adhesive, high-tack silicone adhesive, polyurethane, or other substance. In some embodiments, a bonding adhesive may be formed from an acrylic adhesive with a coating weight of about 15 gsm to about 70 gsm. A bonding adhesive may also be a high-bond strength acrylic adhesive, patterrubber adhesive, high-tack silicone adhesive, or polyurethane, for example. In some embodiments, the bond strength or tackiness of a bonding adhesive may have a peel adhesion or resistance to being peeled from a stainless steel material between about 6 Newtons/25 millimeters (N/mm) to about 10N/25 mm on stainless steel substrate at 23° C. at 50% relative humidity based on the American Society for Testing and Materials ("ASTM") standard ASTM D3330.

The bonding adhesive 128 may be a continuous layer of material or may be a layer with apertures (not shown). The apertures may be formed after application of the bonding adhesive 128 or may be formed by coating the bonding adhesive 128 in patterns on a carrier layer. The apertures may be sized to help control the resultant tackiness of the bonding adhesive 128. The apertures may also be sized to enhance the MVTR of the sealing tape 124. The bonding adhesive 128 may couple the film layer 126 to the sealing adhesive 130.

The sealing adhesive 130 has a thickness 132 that may be in the range of about 100 microns (μm) to about 1000 microns (μm). A sealing adhesive may be a soft material that provides a good seal with the tissue site 102. A sealing adhesive may be formed of a silicone gel (or soft silicone), hydrocolloid, hydrogel, polyurethane gel, polyolefin gel, hydrogenated styrenic copolymer gels, or foamed gels with compositions as listed, or soft closed cell foams (polyurethanes, polyolefins) coated with an adhesive (e.g., 30 gsm-70 gsm acrylic), polyurethane, polyolefin, or hydrogenated styrenic copolymers. In some embodiments, a sealing adhesive may have a stiffness between about 5 Shore OO and about 80 Shore OO. A sealing adhesive may be hydrophobic or hydrophilic. A sealing adhesive may be an adhesive having a low to medium tackiness, for example, a silicone polymer, polyurethane, or an additional acrylic adhesive. In some embodiments, the bond strength or tackiness of a sealing adhesive may have a peel adhesion or resistance to being peeled from a stainless steel material between about 0.5N/25 mm to about 1.5N/25 mm on stainless steel substrate at 23° C. at 50% relative humidity based on ASTM D3330. A sealing adhesive may achieve the bond strength above after a contact time of less than 60 seconds. Tackiness may be considered a bond strength of an adhesive after a very low contact time between the adhesive and a substrate. In some embodiments, a sealing adhesive may have a tackiness that may be about 30% to about 50% of the tackiness of a bonding adhesive.

The sealing adhesive 130 may be formed with a plurality of apertures 134. The apertures 134 may be numerous shapes, for example, circles, squares, stars, ovals, polygons, slits, complex curves, rectilinear shapes, triangles, or other shapes. Each aperture 134 of the plurality of apertures 134 may have an effective diameter. An effective diameter may be a diameter of a circular area having the same surface area as the aperture 134. The average effective diameter of each aperture 134 may be in the range of about 6 mm to about 50 mm. The apertures 134 may have a uniform pattern or may be randomly distributed on the sealing adhesive 130. For example, in some embodiments, the apertures 134 may be distributed so that the apertures 134 extend to edges of the sealing tape 124. In other embodiments, the apertures 134 may be distributed so that a portion of the sealing adhesive 130 includes no apertures 134.

Figure 4A:
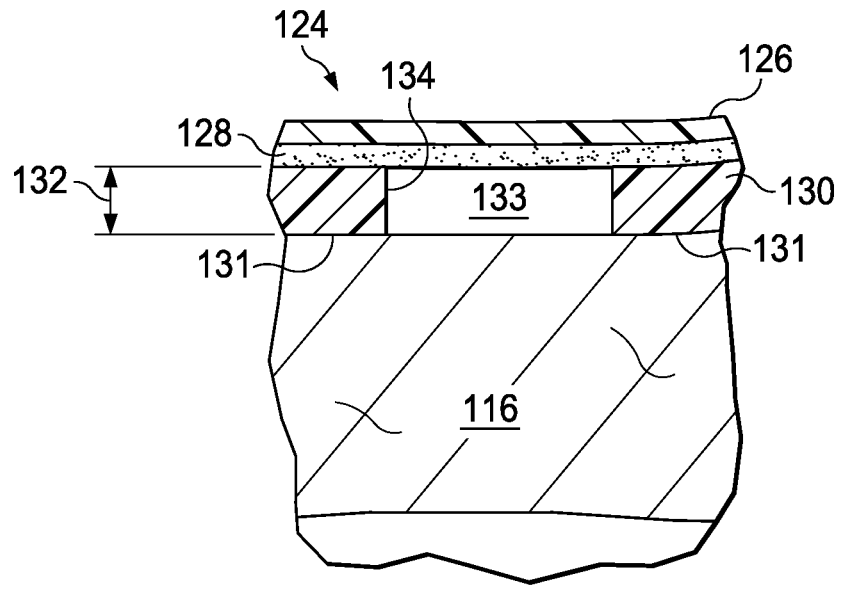
FIG. 4A is a sectional view of a portion of the sealing tape of FIG. 3 with sealing couplings.

FIG. 4A is a sectional view of a portion of the sealing tape 124 illustrating additional details that may be associated with some embodiments. In the assembled state, the bonding adhesive 128 may be coupled to the film layer 126, and the sealing adhesive 130 may be coupled to the bonding adhesive 128. If the sealing adhesive 130 is placed proximate to or in contact with the epidermis 116, the sealing adhesive 130 may form sealing couplings 131 with the epidermis 116. In some embodiments, the thickness 132 of the sealing adhesive 130 may create a gap 133 between the bonding adhesive 128 and the epidermis 116.

Figure 4B:
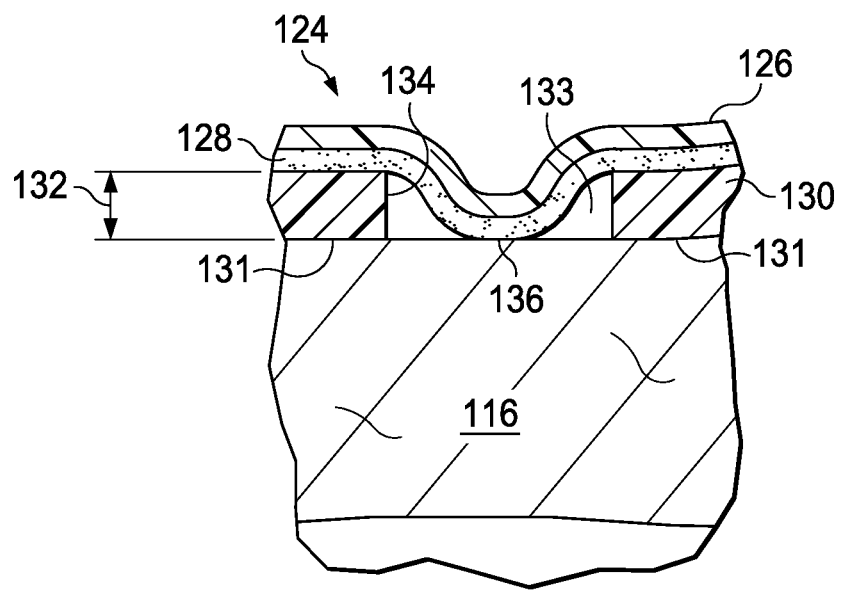
FIG. 4B is a sectional view of the portion of the sealing tape of FIG. 4A with bonding couplings.

FIG. 4B is a sectional view of the sealing tape 124 illustrating additional details that may be associated with some embodiments. If the sealing tape 124 is in a desired location, pressure may be applied to the film layer 126. The pressure may cause the bonding adhesive 128 to be pressed at least partially into contact with the epidermis 116 to form bonding couplings 136. The bonding couplings 136 may provide secure, releasable mechanical fixation to the epidermis 116. The sealing couplings 131 between the sealing adhesive 130 and the epidermis 116 may be sufficient to seal the film layer 126 to the epidermis 116. The sealing couplings 131 may not be as mechanically strong as the bonding couplings 136 between the bonding adhesive 128 and the epidermis 116. The bonding couplings 136 may also anchor the sealing tape 124 to the epidermis 116, inhibiting migration of the sealing tape 124 and the sealing adhesive 130.

The average effective diameter of the apertures 134 of the sealing adhesive 130 may be varied as one control of the tackiness or adhesion strength of the sealing tape 124. In this regard, there is interplay between three main variables for each embodiment: the thickness 132, the average effective diameter of the plurality of apertures 134, and the tackiness of the bonding adhesive 128. The more bonding adhesive 128 that extends through the apertures 134, the stronger the bond of the bonding coupling 136. The smaller the thickness 132 of the sealing adhesive 130, the more bonding adhesive 128 generally extends through the apertures 134 and the greater the bond of the bonding coupling 136. As an example of the interplay, if a very tacky bonding adhesive 128 is used and the thickness 132 of the sealing adhesive 130 is small, the average effective diameter of the plurality of apertures 134 may be relatively smaller. In some embodiments, the thickness 132 may be approximately 200 microns, the bonding adhesive 128 may be approximately 30 microns, have a tackiness of 2000 g/25 cm wide strip, and the average effective diameter may be about 6 mm.

Figure 5:
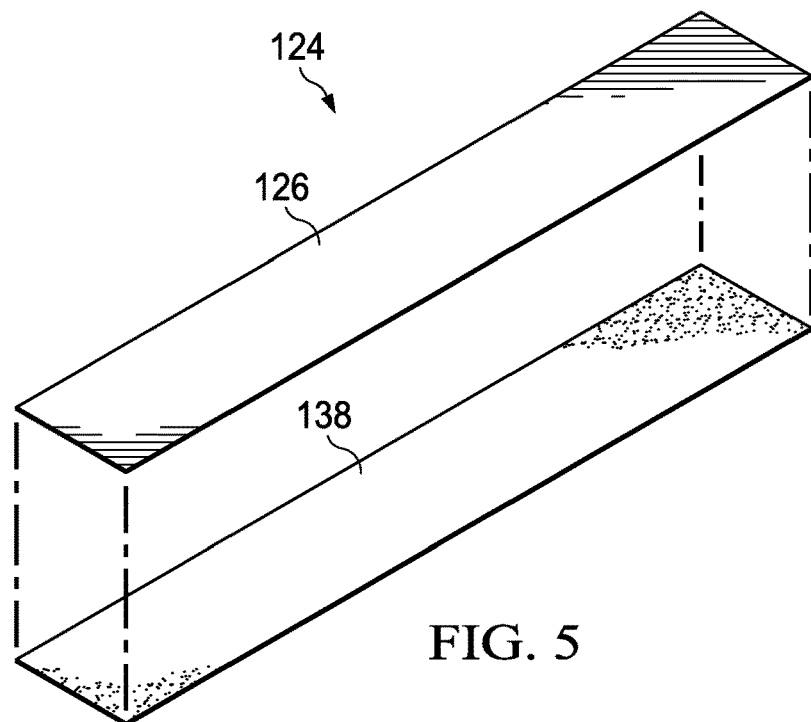
FIG. 5 is an exploded perspective view of a sealing tape that may be used with the systems of FIG. 1A and FIG. 2A.

FIG. 5 is an exploded perspective view of the sealing tape 124 illustrating additional details that may be associated with some embodiments. The sealing tape 124 may include the film layer 126 and an adhesive layer 138 adjacent to the film layer 126.

Figure 6:
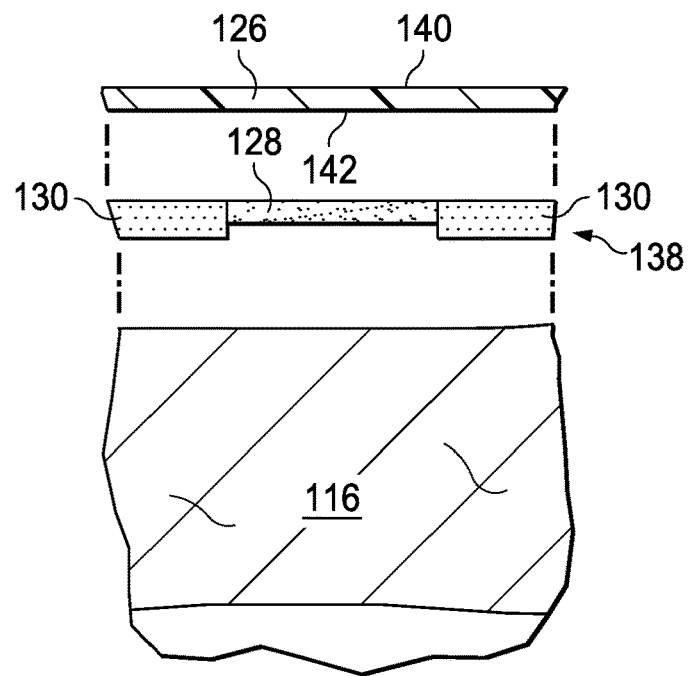
FIG. 6 is a sectional view of a portion of the sealing tape of FIG. 5 proximate to an epidermis.

FIG. 6 is an exploded cross sectional view of the sealing tape 124 illustrating additional details that may be associated with some embodiments. The film layer 126 may have a first side 140 and a second side 142. The adhesive layer 138 may be coupled to the second side 142 of the film layer 126. The adhesive layer 138 may be a medically-acceptable, pressure-sensitive adhesive, glue, bonding agent, or cement, for example. In some embodiments, two adhesives having different characteristics may be used to form the adhesive layer 138. For example, the adhesive layer 138 may include a first adhesive such as the bonding adhesive 128 and a second adhesive such as the sealing adhesive 130. In some embodiments, the placement of the bonding adhesive 128 and the sealing adhesive 130 may be coordinated so that the bonding adhesive 128 and the sealing adhesive 130 both couple directly to the second side 142 of the film layer 126.

The bonding adhesive 128 may be disposed on the film layer 126 in a pattern and may be about 30 microns to about 60 microns in thickness. In a non-limiting illustrative example, the bonding adhesive 128 of the adhesive layer 138 comprises an acrylic adhesive with coating weight of 15 grams/m$^2$ (gsm) to 70 grams/m$^2$ (gsm). In some embodiments, the sealing adhesive 130 may be disposed on the film layer 126 in a pattern and may be about 100 microns to about 400 microns thick. In some embodiments, the adhesive layer 138 may partially cover the second side 142 of the film layer 126, leaving portions of the second side 142 of the film layer 126 free of adhesive. In other embodiments, the adhesive layer 138 may be coextensive with the second side 142 of the film layer 126.

Figure 7:
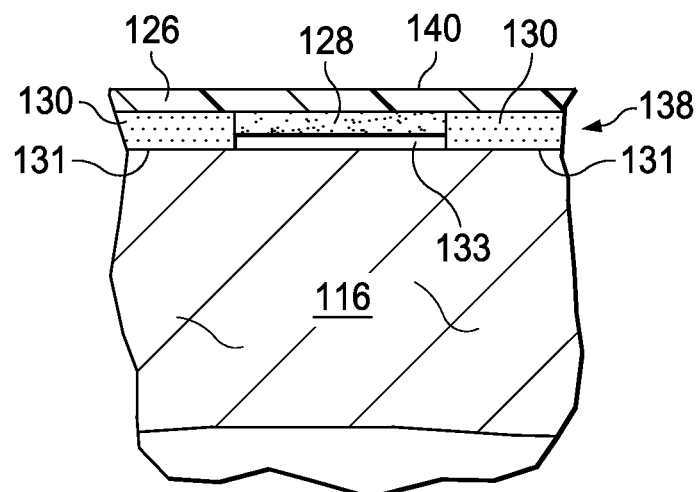
FIG. 7 is a sectional view of the portion of the sealing tape of FIG. 6 with sealing couplings.

FIG. 7 is a sectional view of the sealing tape 124 illustrating additional details that may be associated with some embodiments. In some embodiments, the thickness of the bonding adhesive 128 may be less than the thickness of the sealing adhesive 130 so that the adhesive layer 138 may have a varying thickness. If the adhesive layer 138 is applied to the epidermis 116, the sealing adhesive 130 may can form the sealing couplings 131 with the epidermis 116. In some embodiments, the thickness of the bonding adhesive 128 may be less than the thickness of the sealing adhesive 130, forming the gap 133 between the bonding adhesive 128 and the epidermis 116.

Figure 8:
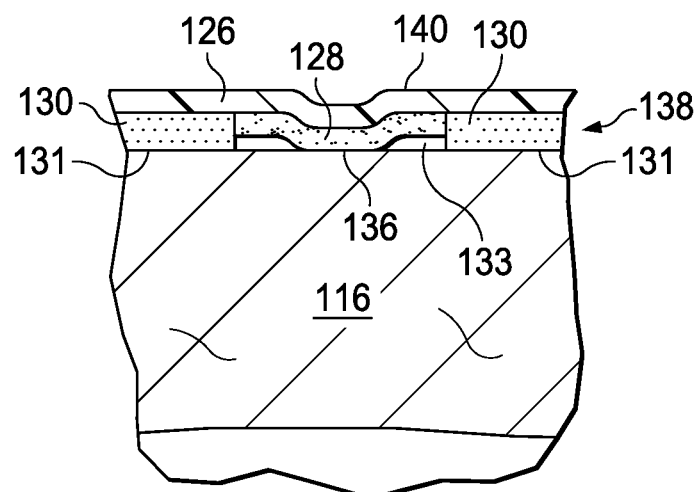
FIG. 8 is a sectional view of the portion of the sealing tape of FIG. 6 with bonding couplings.

FIG. 8 is a sectional view of the sealing tape 124 illustrating additional details that may be associated with some embodiments. If the sealing tape 124 is in a desired location, pressure may be applied to the first side 140 of the film layer 126. The pressure may cause the bonding adhesive 128 to be pressed at least partially into contact with the epidermis 116 to form the bonding couplings 136. The bonding couplings 136 can provide secure, releasable mechanical fixation to the epidermis 116. The sealing couplings 131 between the sealing adhesive 130 and the epidermis 116 may be sufficient to seal the film layer 126 to the epidermis 116. The sealing couplings 131 may not be as mechanically strong as the bonding couplings 136 between the bonding adhesive 128 and the epidermis 116.

According to an illustrative embodiment of the drape 108 in the context of the negative-pressure therapy system 100, the tissue interface 110 may be disposed proximate to the tissue site 102. In some embodiments, the drape 108 may be disposed over the tissue interface 110 and the epidermis 116 to form the sealed therapeutic environment 118. The sealing tape 124 may be applied to the edge of the drape 108 so that a width of each sealing tape 124 overlaps an edge of the drape 108. In some embodiments, each sealing tape 124 may partially cover the drape 108 and partially cover the epidermis 116. The bonding adhesive 128 of the sealing tape 124 may form bonding couplings 136 with the epidermis 116 and a top surface of the drape 108, while the sealing adhesive 130 may form sealing couplings 131 with the epidermis 116 and the top surface of the drape 108. In some embodiments, the bonding couplings 136 may have a peel force against the epidermis 116 between about 0.5N/25 mm to about 2N/25 mm. In this manner, the sealing tape 124 may seal the edges of the drape 108, decreasing leaks between the drape 108 and the epidermis 116.

In another illustrative embodiment, the tissue interface 110 may be disposed proximate to the tissue site 102. One or more sealing tape 124 may be disposed around the tissue site 102 to form the window 125 containing the tissue site 102. The sealing adhesive 130 of each sealing tape 124 may form the sealing couplings 131 with the epidermis 116, and the bonding adhesive 128 of each sealing tape 124 may form the bonding couplings 136 with the epidermis 116. In some embodiments, the bonding couplings 136 may have a peel force against the epidermis 116 between about 0.5N/25 mm to about 2N/25 mm. The drape 108 may be disposed over the tissue interface 110 and the epidermis 116 and coupled to the sealing tape 124 to form the sealed therapeutic environment 118. The bonding couplings 136 and the sealing couplings 136 of the sealing tape 124 may seal the sealing tape 124 to the epidermis 116. The drape 108 may be coupled to the film layer 126 of the sealing tape 124. The first surface 140 of the film layer 126 may provide a bonding surface that is more suitable for adhesion by the standard adhesive of the drape 108 than the epidermis 116. In this manner, the sealing tape 124 may decrease instances of leaks between the drape 108 and the epidermis 116.

As shown in FIG. 6, FIG. 7, and FIG. 8, the pattern of the bonding adhesive 128 and the pattern of the sealing adhesive 130 may be registered. Registration of the bonding adhesive 128 and the sealing adhesive 130 generally refers to the alignment of the two adhesives relative to one another. In particular, registration of the bonding adhesive 128 and the sealing adhesive 130 may refer to the coordination of adhesive placement on the film layer 126 to achieve a desired effect. For example, a certain percentage of overlap of one adhesive over the other adhesive, minimal overlap of one adhesive over the other adhesive so that the adhesives are offset from one another, or complete overlap of one adhesive over the other adhesive are all adhesive placements that may be considered registered. For example, the bonding adhesive 128 and the sealing adhesive 130 may be registered by being disposed on the second side 142 of the film layer 126 so that the bonding adhesive 128 and the sealing adhesive 130 each substantially couple to the second side 142 of the film layer 126. In addition, the bonding adhesive 128 and the sealing adhesive 130 of the example may be aligned relative to one another to have minimal overlap of one adhesive over the other adhesive. In another example, the sealing adhesive 130 may be offset from the bonding adhesive 128, with both adhesives being coupled to the second side 142 of the film layer 126. Registering the bonding adhesive 128 and the sealing adhesive 130 can provide for easier manufacturing and use of the sealing tape 124. Registering of the bonding adhesive 128 and the sealing adhesive 130 may also enhance desired properties of the sealing tape 124 as described in more detail below. Illustrative, but non-limiting, examples of the registration of the bonding adhesive 128 and the sealing adhesive 130 may be described in more detail with respect to the following embodiments.

Figure 9:
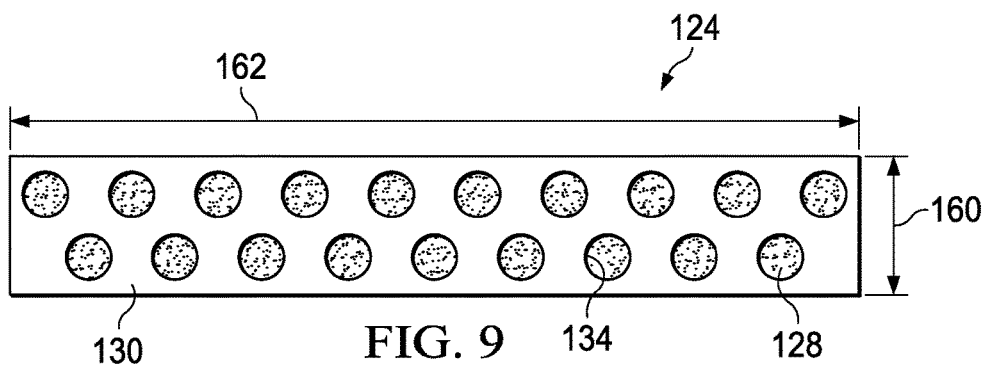
FIG. 9, FIG. 10, FIG. 11, FIG. 12, FIG. 13, FIG. 14, and FIG. 15 are plan views of illustrative patterns of the sealing tape of FIG. 3 and FIG. 5.

FIG. 9 is a plan view of the sealing tape 124 illustrating additional details that may be associated with some embodiments. The sealing tape 124 may have a width 160 and a length 162. In some embodiments, the width 160 may be between about 20 mm. In other embodiments, the width 160 may be between about 10 mm to about 30 mm. In some embodiments, the length 162 may be up to about 200 mm. The sealing tape 124 may be cut or torn so that a sealing tape 124 having the length 162 suitable for use may be provided. For example, a sealing tape 124 may be provided in rolls, allowing a clinician to select a length suitable for a particular tissue site and cut or tear an end of the sealing tape 124 to remove it from the roll. The sealing tape 124 may also include the bonding adhesive 128 and the sealing adhesive 130 having apertures 134. In some embodiments, the bonding adhesive 128 may have a coating weight of about 25 gsm. In some embodiments, the sealing adhesive 130 may have a coating weight of about 100 gsm to about 600 gsm. In some embodiments, the apertures 134 may have a diameter between about 7 mm to about 10 mm. In other embodiments, the apertures 134 may have a diameter between about 5 mm to about 30 mm. In some embodiments, the sealing tape 124 may include two rows of apertures 134 that may be offset from one another. In some embodiments, the apertures 134 may be evenly distributed on the sealing tape 124.

Figure 10:
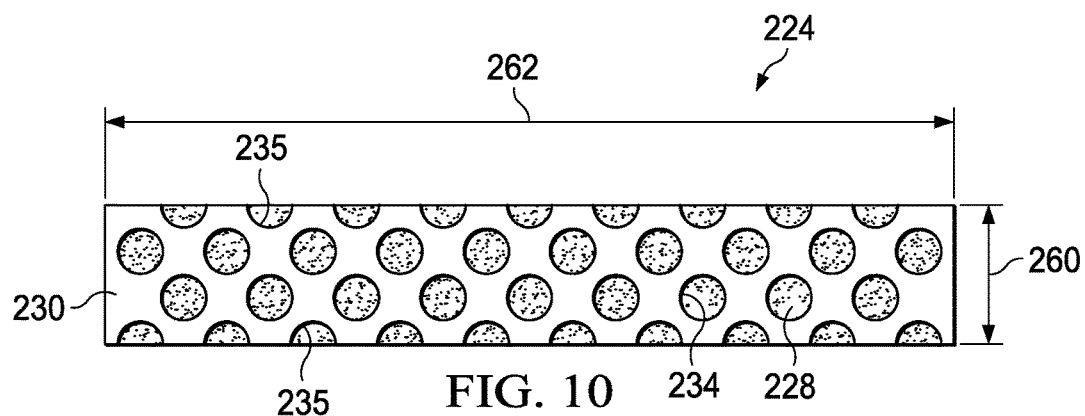

FIG. 10 is a plan view of a sealing tape 224 illustrating additional details that may be associated with some embodiments. The sealing tape 224 may be similar to and operate in a manner similar to the sealing tape 124 of FIG. 9. Similar elements have been indexed to 200. For example, the sealing tape 224 may have a width 260, a length 262, a layer of a bonding adhesive 228, a layer of a sealing adhesive 230, and apertures 234. The apertures 234 may be positioned similar to the apertures 134. In some embodiments, the sealing adhesive 230 of the sealing tape 224 may include edge apertures 235. If the apertures 234 are circles, as shown, the edge apertures 235 may be semi-circles having a radius equal to a radius of the apertures 234. The edge apertures 235 may be positioned so that a diameter of each edge aperture 235 is adjacent to an edge of the sealing tape 224 that is parallel to the length 262. In some embodiments, the edge apertures 235 may be disposed along both edges. In other embodiments, the edge apertures 235 may only be disposed along one edge. The apertures 234 and the edge apertures 235 may be evenly distributed on the sealing tape 224. For example, each aperture 234 and edge aperture 235 may be separated from adjacent apertures 234 and edge apertures 235 by a same distance. In some embodiments, an even distribution may produce a sealing tape 224 having apertures 234 and apertures 235 extending between edges of the sealing tape 224 at regularly repeating distances. The apertures 235 may expose a portion of the bonding adhesive 228 at the edges of the sealing tape 224. Exposure of the bonding adhesive 228 proximate to the edge of the sealing tape 224 may aid in resistance to edge lifting during use of the sealing tape 224. Edge lifting may be the lifting of a portion of the sealing tape 224 when the edge of the sealing tape 224 is caught by clothing or other objects.

Figure 11:
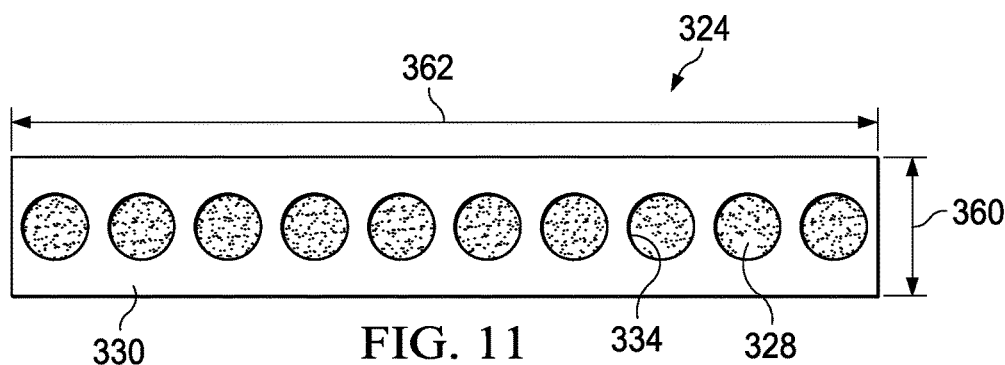

FIG. 11 is a plan view of a sealing tape 324 illustrating additional details that may be associated with some embodiments. The sealing tape 324 may be similar to and operate in a manner similar to the sealing tape 124 of FIG. 9. Similar elements have been indexed to 300. For example, the sealing tape 324 may have a width 360, a length 362, a layer of a bonding adhesive 328, a layer of a sealing adhesive 330, and apertures 334. In some embodiments, the apertures 134 may have a diameter between about 10 mm and about 15 mm. In other embodiments, the apertures 334 may have a diameter between about 5 mm and about 30 mm. In some embodiments, the sealing tape 324 may include a single row of apertures 334. In some embodiments, the apertures are disposed near a center of the width 360 of the sealing tape 334 and may be evenly distributed parallel to the length 362 of the sealing tape 334.

Figure 12:
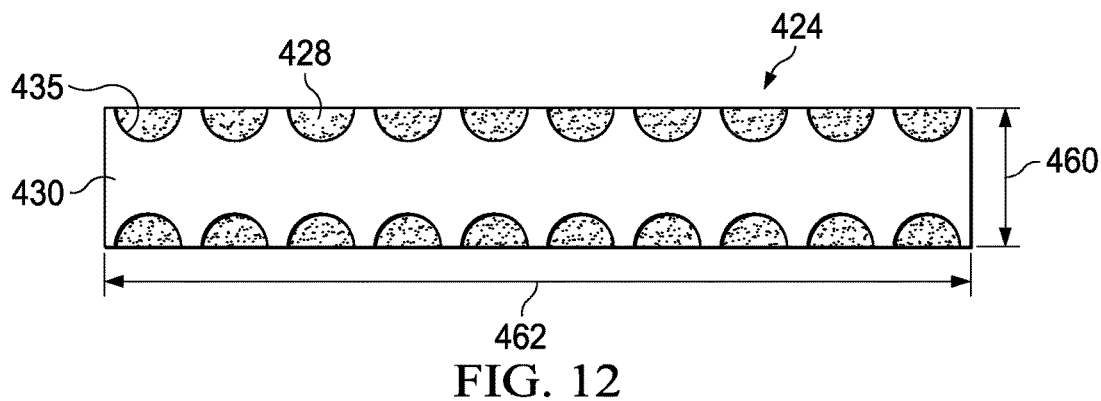

FIG. 12 is a plan view of a sealing tape 424 illustrating additional details that may be associated with some embodiments. The sealing tape 424 may be similar to and operate in a manner similar to the sealing tape 224 of FIG. 10. Similar elements have been indexed to 400. For example, the sealing tape 424 may have a width 460, a length 462, a layer of a bonding adhesive 428, a layer of a sealing adhesive 430, and apertures 435. The apertures 435 may be positioned similar to the apertures 235 and have a radius equal to a radius of the apertures 334.

Figure 13:
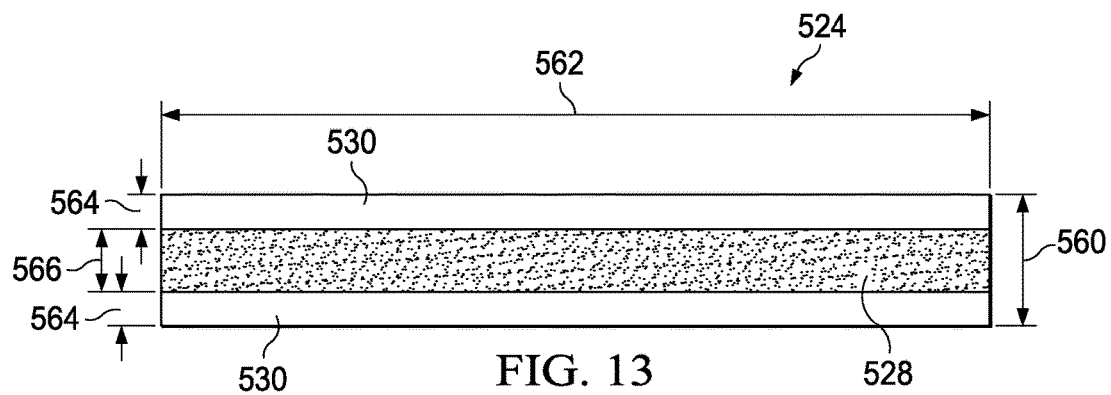

FIG. 13 is a plan view of a sealing tape 524 illustrating additional details that may be associated with some embodiments. The sealing tape 524 may be similar to and operate in a manner similar to the sealing tape 124 of FIG. 9. Similar elements have been indexed to 500. For example, the sealing tape 524 may have a width 560, a length 562, a strip of a bonding adhesive 528, and a strip of a sealing adhesive 530. In some embodiments, the sealing tape 524 may include two strips of the sealing adhesive 530 disposed adjacent to an edge of the sealing tape 524. The two strips of the sealing adhesive 530 may be parallel to the length 562. In some embodiments, the two strips of the sealing adhesive 530 may each have a width 564. In some embodiments, the width 564 of each strip of the sealing adhesive 530 may be between about 5 mm and about 7 mm. In some embodiments, a width 566 of the bonding adhesive 528 exposed through the sealing adhesive 530 may be between about 6 mm and about 10 mm.

Figure 14:
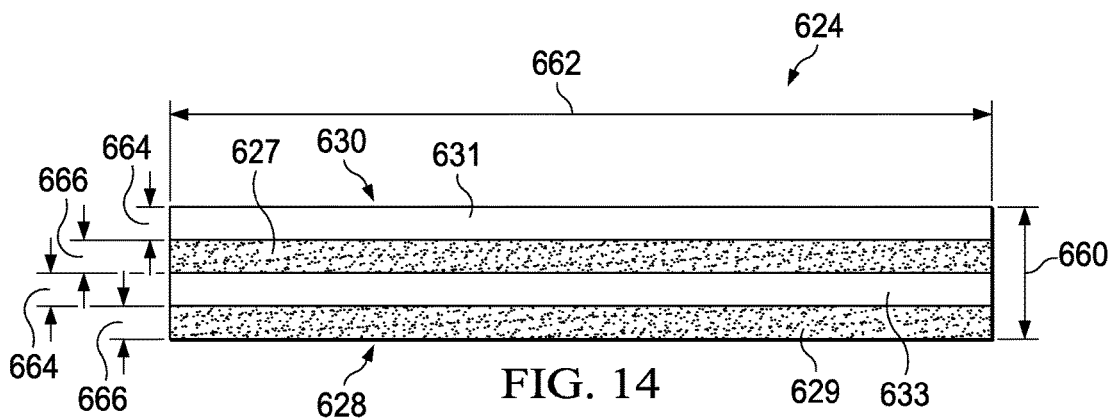

FIG. 14 is a plan view of a sealing tape 624 illustrating additional details that may be associated with some embodiments. The sealing tape 624 may be similar to and operate in a manner similar to the sealing tape 524 of FIG. 13. Similar elements have been indexed to 600. For example, the sealing tape 624 may have a width 660, a length 662, one or more strips of a bonding adhesive 628, and one or more strips of a sealing adhesive 630. In some embodiments, the sealing tape 624 may include two strips of the sealing adhesive 630. In some embodiments, a first strip 631 of the sealing adhesive 630 may be disposed adjacent to an edge of the sealing tape 624. A second strip 633 of the sealing adhesive 630 may be disposed between the edges of the sealing tape 624. The first strip 631 and the second strip 633 of the sealing adhesive 630 may be parallel to the length 662. In some embodiments, the first strip 631 and the second strip 633 of the sealing adhesive 630 may each have a width 664. In some embodiments, the width 664 may be between about 5 mm and about 7 mm. In some embodiments, the portion of the bonding adhesive 628 exposed through the sealing adhesive 630 may include a first strip 627 and a second strip 629. The first strip 627 may be disposed between the first strip 631 and the second strip 633 of the sealing adhesive 630. The second strip 629 may be disposed adjacent to an edge of the sealing tape 624 opposite the first strip 631. In some embodiments, a width 666 of each of the first strip 627 and the second strip 629 of the bonding adhesive 628 exposed through the sealing adhesive 630 may be between about 3 mm and about 5 mm. In some embodiments, the sealing tape 624 may be applied so that the second strip 629 of the bonding adhesive 628 may be in contact with the epidermis 116 to form bonding couplings 136 with the epidermis. The first strip 627 of the bonding adhesive 628 may be in contact with the drape 108 to form bonding couplings 136 with the drape 108.

Figure 15:
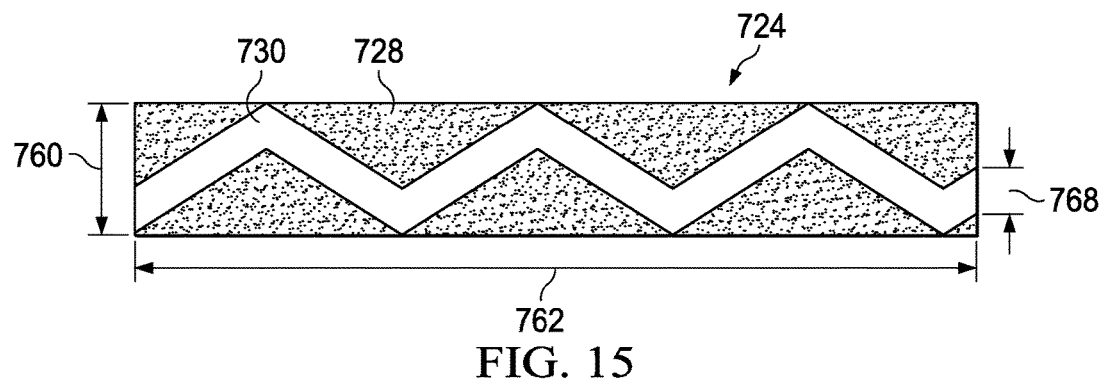

FIG. 15 is a plan view of a sealing tape 724 illustrating additional details that may be associated with some embodiments. The sealing tape 724 may be similar to and operate in a manner similar to the sealing tape 124 of FIG. 9. Similar elements have been indexed to 700. For example, the sealing tape 724 may have a width 760, a length 762, a bonding adhesive 728, and a sealing adhesive 730. In some embodiments, the sealing adhesive 730 may trace a path between opposite edges of the sealing tape 724. The sealing adhesive 730 may propagate parallel to the length 762. For example, the sealing adhesive 730 may have a pattern similar to a wave. In some embodiments, the sealing adhesive 730 may have a regular wave pattern with a repeating slope between each edge of the sealing tape 724. In some embodiments, the sealing adhesive 730 may have a width 768. In some embodiments, the width 768 may be between about 5 mm and about 7 mm.

Any of the above patterns may be manufacturing by layering the adhesives as described above with respect to FIG. 3, FIG. 4A, and FIG. 4B or by registering the adhesives as described above with respect to FIG. 5, FIG. 6, FIG. 7, and FIG. 8.

In some embodiments, the adhesives may be mixed with blowing or expanding agents, for example organic and inorganic low temperature boiling point liquids. The blowing or expanding agents allow for the adhesives to expand under the application of heat or light to increase the thickness of the adhesive following deposition by one of the above described processes. The blowing or expanding agents may reduce the amount of adhesive needed and decrease the cost of production and the cost of the resulting sealing tape 124. In some embodiments, the application of heat or light may be delayed until application of the sealing tape 124 to the epidermis 116 so that the contact area with the patient's epidermis 116 may increase as the bonding adhesive 128 and the sealing adhesive 130 warm by contact with the patient's epidermis 116. The application of light or heat following application of the sealing tape 124 to the epidermis 116 can provide a better seal for some embodiments of the sealing tape 124 to the epidermis 116.

In testing performed with sealing tape in accordance with the embodiments described herein, leaks between a standard drape and a textured surface were reduced. A drape was disposed over the textured surface to create a sealed space. The drape was fluidly coupled to a negative-pressure source. The negative-pressure source was operated and a pressure was measured in the sealed space. When the pressure was measured, the negative-pressure source was unable to achieve 125 mm Hg negative pressure. A leak of about 2 L/m was determined to exist between the standard drape and the textured surface.

Sealing tape in accordance with the embodiments described herein were applied to the edges of the drape. The negative-pressure source was again operated and the pressure measured in the sealed space. By using the sealing tape, the negative-pressure source was able to achieve the therapy pressure of 125 mm Hg and the leak was reduced to 0.08 L/m. The textured surface was then heated, further reducing the leak to 0.01 L/m.

Sealing tape in accordance with the embodiments described herein were also disposed directly on the texture surface. The standard drape was disposed over the textured surface and coupled to the sealing tape to create the sealed space. The textured surface was heated to mimic a patient's body heat. The standard drape was fluidly coupled to the negative-pressure source. The negative-pressure source was operated and a pressure was measured in the sealed space. The negative-pressure source was able to achieve 125 mm Hg negative pressure and the leak was reduced to 0.003 L/m.

The sealing tape may provide a lower cost solution to improving the sealing of standard drapes. The sealing tape may be added to current dressings with low disruption to production or use. The sealing tape also provide a step-change improvement in sealing with a pre-applied dressing using existing materials prior to release from a facility. The sealing tape may also later be used under a drape on re-application of the dressing to provide a seal to a tissue site. The sealing tape may also provide an increased efficiency of adhesive usage as less silicone adhesive may be needed to retain the silicone adhesive in place and under compression with the acrylic adhesive.

Although illustrative, non-limiting embodiments have been disclosed, it should be understood that various changes, substitutions, permutations, and alterations can be made without departing from the scope of the appended claims. It will be appreciated that features that may be described in connection to one embodiment may also be applicable to other embodiments. It will also be understood that the benefits and advantages described above may relate to one embodiment or may relate to several embodiments. It will further be understood that reference to "an" item refers to one or more of those items.

The steps of the methods described herein may be carried out in a suitable order, or simultaneously where appropriate.

Where appropriate, aspects of the embodiments described above may be combined with aspects of the other embodiments described to form further examples having comparable or different properties and addressing the same or different problems.

It will be understood that the embodiments described herein are given by way of example only and that various modifications may be made by those skilled in the art. The above specification, examples and data provide a complete description of the structure and use of exemplary embodiments. Although various embodiments have been described above with a certain degree of particularity, or with reference to one or more individual illustrations, those skilled in the art could make numerous alterations to the example embodiments without departing from the scope of the claims.

We claim:

1. A dressing for treating a tissue site with negative pressure, the dressing comprising:
   a tissue interface configured to be positioned adjacent to the tissue site;
   a sealing member configured to be positioned over the tissue interface and the tissue site to form a sealed environment; and
   a sealing tape comprising:
      a bonding adhesive layer comprising a bonding adhesive disposed in a continuous layer and having a high-bond strength; and
      a sealing adhesive layer comprising a sealing adhesive disposed in a continuous layer and having a low-bond strength, the sealing adhesive layer having portions removed to expose the bonding adhesive layer through the sealing adhesive layer, the sealing tape being elongated and configured to attach the sealing member to epidermis,
      wherein the bonding adhesive layer and the sealing adhesive layer are coincident.

2. The dressing of claim 1, wherein the sealing tape is configured to be coupled over edges of the sealing member so that the sealing tape is partially coupled to the epidermis and partially coupled to the sealing member.

3. The dressing of claim 1, wherein the sealing tape is configured to be coupled to the epidermis adjacent to the tissue site and the sealing member is coupled to the sealing tape so that the sealing tape is between the sealing member and the epidermis.

4. The dressing of claim 1, wherein the sealing tape further comprises:
   a film layer coupled to the bonding adhesive; and
   the sealing adhesive layer is coupled to the bonding adhesive layer, the portions removed forming a first pattern and exposing the bonding adhesive layer in a second pattern.

5. The dressing of claim 4, wherein the first pattern comprises a layer having at least one row of apertures disposed proximate a center of the sealing tape and the second pattern comprises remaining portions of the sealing tape.

6. The dressing of claim 4, wherein the first pattern comprises a layer having at least two rows of apertures and the second pattern comprises remaining portions of the sealing tape.

7. The dressing of claim 6, wherein the rows of apertures are offset from each other.

8. The dressing of claim 4, wherein:
   the first pattern comprises a layer having a first plurality of apertures disposed in a pattern on the sealing tape and a second plurality of apertures having shapes that are a portion of shapes of the first plurality of apertures, the second plurality of apertures disposed adjacent to an edge of the sealing tape; and
   the second pattern comprises the remaining portions of the sealing tape.

9. The dressing of claim 8, wherein the first plurality of apertures have a circular shape and the second plurality of apertures have a semi-circular shape.

10. The dressing of claim 4, wherein the first pattern comprises a plurality of apertures positioned adjacent to edges of the sealing tape and the second pattern comprises the remaining portions of the sealing tape.

11. The dressing of claim 1, wherein the sealing tape further comprises an expanding agent mixed with at least one of the bonding adhesive and the sealing adhesive.

12. A system for treating a tissue site with negative-pressure, the system comprising:
   a manifold configured to be positioned adjacent to the tissue site;
   a drape configured to be positioned over the tissue site and the manifold and seal to tissue adjacent to the tissue site to form a sealed space;
   a negative-pressure source configured to provide negative-pressure to the sealed space; and
   a sealing tape configured to be coupled to the drape and epidermis, the sealing tape being elongated and comprising:

a bonding adhesive layer coupled to a side of the sealing tape, the bonding adhesive layer comprising a bonding adhesive disposed in a continuous layer and having a high-bond strength; and a sealing adhesive layer comprising a sealing adhesive disposed in a continuous layer and having a low-bond strength, the sealing adhesive layer coupled to the bonding adhesive layer and having portions removed to expose the bonding adhesive layer through the sealing adhesive layer, wherein the bonding adhesive layer and the sealing adhesive layer are coincident.

13. The system of claim 12, wherein the sealing tape is configured to be coupled over edges of the drape so that each sealing tape is partially coupled to the epidermis and partially coupled to the drape.

14. The system of claim 12, wherein the sealing tape is configured to be coupled to the epidermis and the drape is coupled to the sealing tape so that the sealing tape is between the drape and the epidermis.

15. The system of claim 12, wherein the sealing tape further comprises:

a film layer coupled to the bonding adhesive layer; and the portions removed to forming a first pattern and exposing the bonding adhesive layer in a second pattern.

16. The system of claim 15, wherein the first pattern comprises a layer having at least one row of apertures disposed proximate a center of the sealing tape and the second pattern comprises remaining portions of the sealing tape.

17. The system of claim 15, wherein the first pattern comprises a layer having at least two rows of apertures and the second pattern comprises remaining portions of the sealing tape.

18. The system of claim 17, wherein the rows of apertures are offset from each other.

19. The system of claim 15, wherein:

the first pattern comprises a layer having a first plurality of apertures disposed in a pattern on the sealing tape and a second plurality of apertures having shapes that are a portion of shapes of the first plurality of apertures, the second plurality of apertures disposed adjacent to an edge of the sealing tape; and the second pattern comprises the remaining portions of the sealing tape.

20. The system of claim 19, wherein first plurality of apertures have a circular shape and the second plurality of apertures have a semi-circular shape.

21. The system of claim 15, wherein the first pattern comprises a layer having a plurality of apertures positioned adjacent to edges of the sealing tape and the second pattern comprises the remaining portions of the sealing tape.

22. The system of claim 12, wherein the sealing tape further comprises an expanding agent mixed with at least one of the bonding adhesive and the sealing adhesive.

* * * * *

UNITED STATES PATENT AND TRADEMARK OFFICE
CERTIFICATE OF CORRECTION

PATENT NO. : 10,946,124 B2
APPLICATION NO. : 14/517521
DATED : March 16, 2021
INVENTOR(S) : Locke et al.

Page 1 of 1

It is certified that error appears in the above-identified patent and that said Letters Patent is hereby corrected as shown below:

In the Claims

Column 20
Line 18 (approx.), In Claim 20, before "first plurality" insert -- the --, therefor.

Signed and Sealed this
Ninth Day of April, 2024

Katherine Kelly Vidal
*Director of the United States Patent and Trademark Office*